United States Patent [19]

Raifeld

[11] Patent Number: 5,153,337
[45] Date of Patent: Oct. 6, 1992

[54] STEREO AND ENANTIOSELECTIVE SYNTHESIS OF TETRAHYDRO-5-SUBSTITUTED-3-METHYLENE-2-FURANMETHANOLS

[75] Inventor: Yuri E. Raifeld, Moscow, U.S.S.R.

[73] Assignee: American Cyanamid Company, Wayne, N.J.

[21] Appl. No.: 698,041

[22] Filed: May 10, 1991

[51] Int. Cl.$^5$ ............................................ C07D 307/20
[52] U.S. Cl. ...................................... 549/475; 549/555
[58] Field of Search ................................ 549/475, 555

[56] References Cited

U.S. PATENT DOCUMENTS 4,772,727 9/1988 Sutherland et al. ................. 549/555

FOREIGN PATENT DOCUMENTS 0029678 2/1984 Japan.
0034961 2/1985 Japan.

OTHER PUBLICATIONS

Fleet, G. W., Tetrahedron, 1988, 44(2) 625-636.
Bravo, P. et al., J. Org. Chem., 1989, 54: 5171-5176.
Y. Gao et al., J. Amer. Chem. Soc., 1987, 109: 5665-5780.
Kochetkov, N. K. et al., Tetrahedron Lett., 1981, 22(43): 4315-4318.

*Primary Examiner*—C. Warren Ivy
*Assistant Examiner*—Amelia A. Owens
*Attorney, Agent, or Firm*—Kenneth J. Dow

[57] ABSTRACT

Novel processes and intermediates for the preparation of tetrahydro-5-hydroxy-3-methylene-2-furan-methanol and of tetrahydro-5-[lower alkoxy ($C_1$-$C_3$)]-3-methylene-2-furanmethanol useful as intermediates in the synthesis of various modified nucleosides having antiviral and other biological activity.

18 Claims, No Drawings

STEREO AND ENANTIOSELECTIVE SYNTHESIS OF TETRAHYDRO-5-SUBSTITUTED-3-METHYLENE-2-FURANMETHANOLS

FIELD OF THE INVENTION

The present invention is directed to novel processes and intermediates for the preparation of tetrahydro-5-hydroxy-3-methylene-2-furanmethanol and of tetrahydro-5-[lower alkoxy ($C_1$–$C_3$)]-3-methylene-2-furanmethanol useful as intermediates in the synthesis of various modified nucleosides having biological activity.

BACKGROUND OF THE INVENTION

The recent discovery of the reverse transcriptase inhibiting activity of various modified nucleosides and their actual and potential utility as therapeutic agents in the treatment of Acquired Immunodeficiency Syndrome (AIDS) related human immunodeficiency virus (HIV) infections, has stimulated interest in improved methods of preparing such modified nucleosides. Of particular interest are new methods of preparing 3'-azido-3'-deoxythymidine (AZT) and 3'-deoxy-3'-fluorothymidine (FLT) which have been reported to be potent inhibitors of HIV-induced cytopathogenicity. Extensive studies on the synthesis and biological activity of 3'-azido, 3'-amino, and 3'fluoro pyrimidine and purine 2',3'dideoxyribonucleoside analogues have been reported.

In general, methods of producing such 3'-substituted nucleosides have proceeded along two separate paths: (1) substitution of the 3'-OH function in a 2'-deoxynucleoside, as in the case of the synthesis of AZT or FLT from thymidine, or (2) preparation of a 3-substituted furanoside compound followed by the coupling of a suitable purine or pyrimidine base such as thymine. The latter method has certain advantages since it uses simpler starting materials and it provides for the easy substitution of a number of nucleophiles at the 3'-position to provide intermediates suitable for efficient coupling with purine or pyrimidine bases. The latter method therefore provides the greatest possibilities for synthesis of 3'-substituted nucleosides in large scale quantities.

Several methods for the synthesis of 3-substituted furanoside sugars have been described but they are complicated, and they require multiple steps and expensive reagents. Fleet, G. W. et al; *Tetrahedron* 1988, 44(2) 625–636 describes the synthesis of methyl 5-0-tert-butyl-diphenylsilyl-2-deoxy-α(β)-D-threopentofuranoside from D-xylose and its conversion to the azido, fluoro and cyano sugars followed by the subsequent coupling of these derivatives with protected thymine to give the thymidine compounds Bravo, P. et al., *J. Org. Chem.* 1989, 54, 5171–5176 describes the asymmetric synthesis of the 3-fluoro furanose sugars starting from a compound of the formula:

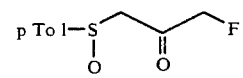

which is monoalkylated on the fluorinated carbon with allyl bromide. Removal of the auxiliary sulfinyl group followed by a reductive work-up and oxidative cleavage of the double bond afforded the 5-0-benzoyl-2,3-dideoxy-3-fluoro-furanose.

Monosaccharides, containing an exocyclic double bond are also valuable, useful compounds for use in the synthesis of branched and functionally substituted carbohydrates. N. K. Kochetkov et al, *Tetrahedron Letters*, 22 (43), 4315–4318 (1981) describes the synthesis of several macrolide antibiotics employing carbohydrates during their synthetic construction.

However, tetrahydro-5-substituted-3-methylene-2-furanmethanols are new and not known as useful intermediates for the synthesis of 3'-substituted nucleosides.

The present invention describes an improved alternate method for the stereo and enantioselective synthesis of tetrahydro-5-hydroxy-3-methylene-2-furanmethanol and of tetrahydro-5-[lower alkoxy ($C_1$–$C_3$)]-3-methylene-2-furanmethanol. The process is new, uncomplicated, uses a small number of steps and simple, inexpensive starting materials.

SUMMARY OF THE INVENTION

This invention is directed to novel tetrahydro-5-hydroxy-3-methylene-2-furanmethanol and tetrahydro-5-[lower alkoxy($C_1$–$C_3$)]-3-methylene-2-furanmethanol of Formula I which are useful as intermediates in the preparation of branched and functionally 3'-substituted nucleosides.

This invention is also related to an improved process for the stereo and enantioselective synthesis of tetrahydro-5-substituted-3-methylene-2-furanmethanols the formula:

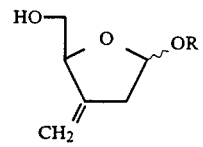

FORMULA 1 wherein R is H or lower alkyl ($C_1$–$C_3$). The improved process may be depicted by the following reaction Scheme I:

SCHEME I

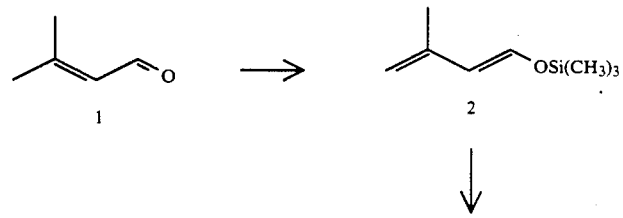

SCHEME I

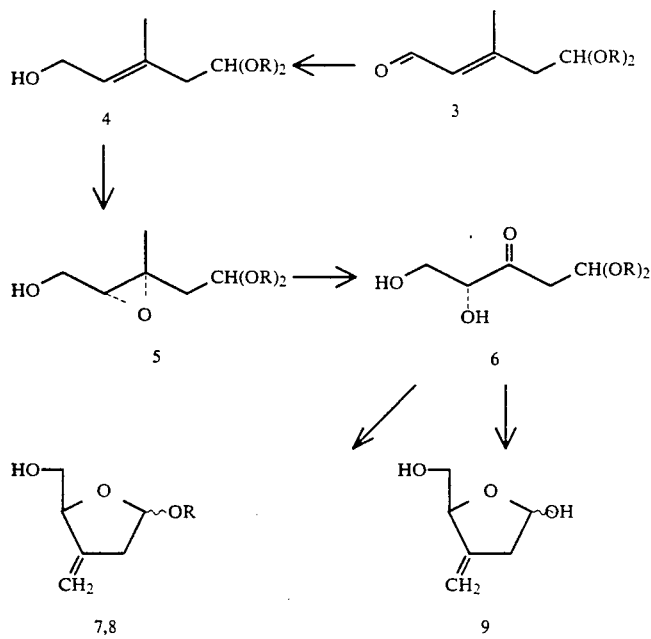

DETAILED DESCRIPTION

In general, 3-methyl-2-butenal 1 is reacted with chlorotrimethylsilane to afford 2. Reaction of 2 with a trialkyl (C₁–C₃) orthoformate yields 3. Reduction of 3 with sodium bis(2-methoxyethoxy)aluminum hydride affords 4. Epoxidation of 4 gives oxirane 5. Treatment of 5 with a catalytic amount of titanium(IV) isopropoxide yields 6. Treatment of 6 with a trace of HCl in ethanol gives a mixture of 7 and 8. Hydrolysis of 6 gives 9.

In accordance with the foregoing Scheme I, the compounds of Formula I are prepared by the following steps:

(a) 3-methyl-2-butenal is reacted with chlorotrimethylsilane using the method of P. Cazeau et al., *Tetrahedron* 43, 2075–2088 (1987), in acetonitrile containing triethylamine and anhydrous sodium iodide at 40°–45° to yield 1-trimethylsilyloxy-3-methyl-1,3-butadiene 2;

(b) compound 2 is reacted with a trialkyl (C₁–C₃) orthoformate in ethyl acetate in the presence of a 15% solution of zinc chloride in ethyl acetate at room temperature over 1 hour to give 1,1-diethoxy-3-methyl-4-pentenal 3;

(c) compound 3 is then reduced at 0° to +5° C. with sodium bis(2-methoxyethoxy)aluminum hydride in toluene to yield allyl alcohol 4, 1,1-diethoxy-3-methyl-4-penten-5-ol;

(d) the allyl alcohol 4 is then asymmetrically epoxidated in the presence of diisopropyl D-(−)-tartrate, titanium(IV) isopropoxide, 4° A sieves and tert-butyl hydroperoxide in methylene chloride at −20° C. to afford the novel oxirane compound 5, trans -(+)-1, 1-diethoxy-3-methyl-3,4-epoxypentan-5-ol;

(e) the oxirane compound 5 is then subjected to ring opening by treatment with a catalytic amount of titanium(IV) isopropoxide in refluxing benzene over 3 hours to give 6, (S)-5,5-diethoxy-3-methylene-1,2-pentanediol.

(f) the diol compound 6 is treated with a 10% solution of HCl in ethanol at room temperature for 30 minutes to afford a mixture of 7 (2S-cis)-tetrahydro-5-ethoxy-3-methylene-2-furanmethanol and 8 (2S-trans)-tetrahydro-5-ethoxy-3-methylene-2-furanmethanol.

(g) the diol compound 6 is treated with an aqueous solution of acid form ion-exchange resin at room temperature for 3 hours to yield compound 9 tetrahydro-5-hydroxy-3-methylene-2-furanmethanol.

As set forth above in Step (d), the allyl alcohol compound 4 is asymmetrically epoxidated by the method of Y. Gao et al., *J. Amer. Chem. Soc.*, 109, 5765–5780 (1987), hereby incorporated by reference into the present application. This method produces epoxides from olefins in at least a 94% enantiomeric excess. Olefins can be converted to the corresponding epoxide on treatment with a catalytic amount of a catalyst prepared from a tartrate such as diethyl or diisopropyl tartrate and titanium(IV) isopropoxide. The best ratio of titanium/tartrate is 1:1.2. It is important to keep the reaction mixture free of moisture. Powdered activated molecular sieves work well. Solvents such dichloromethane, toluene or isooctane can be used. Reactions are generally carried out at temperatures of about −20° C. All reactions are done in the presence of tert-butyl hydroperoxide (TBHP), although other peroxides have been used successfully.

In general, the catalyst is prepared by mixing the chosen tartrate and titanium(IV) isopropoxide at −20° C. in a solvent such as methylene chloride whereupon either the olefinic alcohol or the tert-butyl hydroperoxide is added. In any case, the three ingredients are added and stirred for about 30 minutes before the last reagent is added, whether it be the alcohol or the tert-butyl hydroperoxide. All reactions are carried out in the presence of powdered activated sieves. The 30 minutes of stirring is termed the "aging" period and is an important factor in obtaining high enantioselectivity.

The tetrahydro-5-ethoxy-3-methylene-2-furanmethanol compounds 7 and 8 and the tetrahydro-5-ethoxy-3-methylene-2-furanmethanol compound 9 are useful as precursors for the preparation of various 3'-substituted nucleoside compounds such as 3'-azido-3'-deoxythymidine (AZT) or 3'-deoxy-3-'fluorothymidine (FLT) which have known utility as inhibitors of HIV induced cytopathogenicity. In general, the furanmethanol compounds of Formula I maybe subjected to standard coupling reactions with various azaheterocycles under Lewis acid conditions; for example, trimethylsilyl trifluoromethanesulfonate, zinc chloride or stannic chloride. Alternatively, the furanomethanol (Formula I) maybe further functionalized at the newly-formed olefinic position with electrophilic reagents; for example, hydroboration, osmylation or halohydrin formation.

Upon further study of the specification and appended claims, further objects and advantages of this invention will become apparent to those skilled in the art.

This invention will be described in greater detail in conjunction with the following, non-limiting specific examples.

EXAMPLE 1

1-Trimethylsilyloxy-3-methyl-1,3-butadiene

To a suspension of 180 g of anhydrous sodium iodide in 300 ml of dry acetonitrile is added a solution of 112 g of triethylamine and 84 g of 3-methyl-2-butenal in 400 ml of pentane at room temperature. Added dropwise to the above solution is 109 g of chlorotrimethylsilane at 35°-38° C. and the mixture stirred for 4 hours at 40°-45° C. The resulting solid is filtered, washed with 400 ml of pentane and the solvent evaporated to a residue. The residue is distilled to afford 112 g of the desired product, B.P. 56°-60° C./35 mm, $n_D^{20}$ 1.4496.

Anal. Calc'd for $C_8H_{16}OSi$: C, 61.48; H, 10.32; Si, 17.97. Found: C, 61.59; H, 10.24; Si, 17.68.

EXAMPLE 2

1,1-Diethoxy-3-methyl-4-pentenal

To a mixture 104 g of triethyl orthoformate and a 15% solution of zinc chloride in ethyl acetate is added 109 g of the product of Example 1, dropwise with stirring at room temperature. Following an additional hour of stirring, 600 ml of saturated aqueous sodium bicarbonate is carefully added. The resulting precipitate is filtered and the cake washed with 600 ml of ether. The aqueous phase is separated and the organic phase washed with 200 ml of saturated aqueous sodium bicarbonate, dried with potassium carbonate and evaporated to a residue. The residue is distilled to give 78 g of the desired product as an oil, B. P. 68°-70° C./3 mm, $n_D^{20}$ 1.4590. $^{13}$C-NMR: δ 191.12(C-5), 159.71(C-3), 129.85(C-4), 101.74(C-1), 61.75(OC$_2$H$_5$), 45.13(C-2), 18.13(CH$_3$), 15.46(OC$_2$H$_5$)- trans; 191.20(C-5), 159.04(C-3), 130.27(C-4), 62.61(OC$_2$H$_5$), 38.00(C-2), 26.17(CH$_3$), 15.56(OC$_2$H$_5$)-cis.

Anal. Calc'd for $C_{10}H_{18}O_3$: C,64.49; H, 9.74. Found: C,64.72; H, 9.89.

EXAMPLE 3

1,1-Diethoxy-3-methyl-4-penten-5-ol

To a 30% solution of 200 ml of sodium bis(2-methoxyethoxy)aluminum hydride in toluene at 0° C. is added dropwise with stirring a solution of 50 g of the product of Example 2 in 50 ml of ether. The mixture is stirred for 1 hour at 0° to +5° C. Saturated aqueous ammonium chloride is added dropwise at 0° to +5° C. followed by stirring for 30 minutes at 10° to 15° C. The solid is filtered and washed with 300 ml of ether. The organic phase is separated, dried with potassium carbonate and evaporated to a residue. The residue is vacuum distilled to give 41 g of the desired product as an oil, BP 93°-96° C./0.5 mm, $n_D^{20}$ 1.4550.

$^{13}$C-NMR: δ 133.44(C-3), 128.45(C-4), 102.76(C-1), 61.32(OC$_2$H$_5$) , 58.96(C-5), 44.31(C-2), 16.90(CH$_3$), 15.54(OC$_2$H$_5$) -trans; 134.25(C-3), 128.51(C-4), 102.61(C-1), 62.11(OC$_2$H$_5$), 58.69(C-5), 37.45(C-2), 21.62(CH$_3$), 15.60(OC$_2$H$_5$)-cis.

Anal. Calc'd for $C_{10}H_{20}O_3$: C,63.79; H, 10.71. Found: C,63.71; H, 10.75

EXAMPLE 4

Trans-(+)-1,1-diethoxy-3-methyl-3,4-epoxypentan-5-ol

A mixture of 5 g of powdered, 4° A activated molecular sieves in 300 ml of methylene chloride is cooled to −20° C. Sequentially added are 2.84 g of diisopropyl D-(−)tartrate, 3.51 g of titanium(IV) isopropoxide and 45.5 ml of tert-butyl hydroperoxide followed by stirring at −20° C. for 30 minutes. A solution of 18.8 g of the product of Example 3 in 20 ml of methylene chloride is added. Stirring is maintained at −20° C. for 8 hours followed by the addition of 8 ml of a 10% aqueous sodium hydroxide solution saturated with sodium chloride. At 10° C. is added 8 g of anhydrous magnesium sulfate and 1 g of diatomaceous earth. The mixture is stirred for 15 minutes and allowed to stand for 1 hour. The suspension is filtered through a pad of diatomaceous earth and the cake washed with ether (3×50 ml). The filtrate and washings are combined, dried with anhydrous magnesium sulfate and evaporated to a residue. The residue is purified by column chromatography on silica gel using a hexane-ether gradient elution to afford 13.7 g of the desired product as an oil, $n_D^{20}$ 1.4465, $[\alpha]_D + 19°$ (C 3.5, methanol).

Anal. Calc'd. for $C_{10}H_{20}O_4$: C, 58.80; H, 9.87. Found: C, 58.76; H, 9.88.

EXAMPLE 5

(S)-5,5-Diethoxy-3-methylene-1,2-pentanediol

To a solution of 2.04 g of the product of Example 4 in 80 ml of benzene at 20° C. is added 1.42 g of titanium-(IV) isopropoxide. The mixture is refluxed for 3 hours then cooled to room temperature followed by the addition of 30 ml of ether and 2 ml of saturated aqueous sodium bicarbonate and stirring for 30 minutes. The suspension is filtered through a pad of diatomaceous earth. The pad is washed with ether (3×10 ml) and the solvent evaporated to a residue which is purified by column chromatography on silica gel by elution with 20:1 chloroform-methanol to afford 1.78 g of the desired product as a syrup, $[\alpha]_D + 12°$ (C 2.2, methanol).

Anal. Calc'd for $C_{10}H_{20}O_4$: C, 58.80; H, 9.87. Found: C, 58.83; H, 9.85.

EXAMPLE 6

(2S-cis)-Tetrahydro-5-ethoxy-3-methylene 2-furanmethanol and (2S-trans)-tetrahydro-5-ethoxy-3-methylene-2-furanmethanol To a solution of 1.75g of the product of Example 5 in 230 ml of dry ethyl alcohol is added 0.22 ml of a 10% solution of HCl in ethanol at room temperature. The mixture is stirred for 30 minutes and 0.1 g of potassium carbonate added followed by stirring for 1 hour. The mixture is filtered and the cake washed with dry ether (3×10 ml). The combined filtrates are evaporated and the residue purified by column chromatography on silica gel by elution with chloroform to give 0.84 g of the desired product $[\alpha]_D + 218°$ (C 2.0, methanol).

Anal. Calc'd. for $C_8H_{14}O_3$: C, 60.74; H, 8.92. Found: C, 60.78; H, 8.96.

EXAMPLE 7

(2S-cis)-Tetrahydro-5-hydroxy-3-methylene-2-furanmethanol and (2S-trans)-tetrahydro-5-hydroxy-3-methylene-2-furanmethanol To a solution of 2.04 g of the product of Example 5 in 40 ml of water is added 0.4 g of QU-2 ion-exchange resin. The mixture is stirred for 3 hours at room temperature, filtered and the solid washed with water (2×5 ml). To the combined filtrate and washings is added 0.6 g of barium carbonate. The mixture is stirred for 30 minutes, the solid filtered, and the filtrate evaporated to give 1.09 g of the desired products as a syrup. $[\alpha]_D + 4°$ (C 2.0, $H_2O$).

Anal Calc'd for $C_6H_{10}O_3$: C, 55.37; H, 7.75. Found: C, 55.33; H, 7.70.

We claim:
1. A compound of the formula:

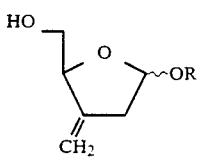

wherein R is H or alkyl ($C_1$–$C_3$).

2. A process for preparing a compound of the formula:

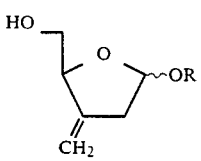

wherein R is H or alkyl ($C_1$–$C_3$);
which comprises reacting 3-methyl-2-butenal with chlorotrimethylsilane to give a silyl ether which is in turn reacted with trialkyl ($C_1$–$C_3$) orthoformate to afford an orthoester which is reduced with sodium bis(2-methoxyethoxy)aluminum hydride to give an allyl alcohol which is epoxidized with a catalytic amount of titanium(IV) isopropoxide to afford an oxirane which is treated with a catalytic amount of titanium(IV) isopropoxide to yield a diol which is treated with hydrochloric acid in an alcohol, to yield a mixture of (2S-cis)-tetrahydro-5-ethoxy-3-methylene-2-furanmethanol and (2 S - trans)-tetrahydro-5-ethoxy-3-methylene-2-furanmethanol or treatment of the diol with an acid form ion-exchange resin to give tetrahydro-5-hydroxy-3-methylene-2-furanmethanol.

3. A process for preparing a compound of the formula:

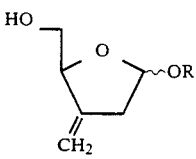

wherein R is H or alkyl ($C_1$–$C_3$); which comprises;
a) reacting 3-methyl-2-butenal with chlorotrimethylsilane in a suitable solvent containing trimethylsilamine and sodium iodide at 40°–50° C. to form 1-trimethylsilyloxy-3-methyl-1,3-butadiene;
b) reacting the product of step a with a trialkyl ($C_1$–$C_3$) orthoformate in the presence of zinc chloride in a suitable solvent at room temperature over 1 hour to form 1,1-diethoxy-3-methyl-4-pentenal;
c) reacting the product of step b with sodium bis(2-methoxyethoxy) aluminum hydride in a suitable solvent to form 1,1-diethoxy-3-methyl-4-penten-5-ol;
d) reacting the product of step c with diisopropyl D-(−)-tartrate, titanium (IV) isopropoxide and tert-butyl h in a suitable solvent at −20° C. to form trans-(+)-1,1-diethoxy-3-methyl-3,4-epoxypentan-5-ol;
e) reacting the product of step d with a catalytic amount of titanium (IV) isopropoxide in a suitable solvent over 3 hours to form (S)-5,5-diethoxy-3-methylene-1,2-pentanediol;
f) reacting the product of step e with 10% HCl in a suitable solvent for 30 minutes to form (2S-cis)-tetrahydro-5-ethoxy-3-methylene-2-furanmethanol and (2S-trans)-tetrahydro-5-ethoxy-3-methylene-2-furanmethanol.
g) reacting the product of step e with acid form ion-exchange resin in aqueous solution at room temperature for 3 hours to form tetrahydro-5-hydroxy-3-methylene-2-furanmethanol; and 4. A process according to claim 3(a), wherein the suitable solvent is acetonitrile.

5. A process according to claim 3(b), wherein the suitable solvent is ethyl acetate.

6. A process according to claim 3(c) wherein the suitable solvent is toluene.

7. A process according to claim 3(d) wherein the suitable solvent is methylene chloride.

8. A process according to claim 3(e) wherein the suitable solvent is benzene.

· 9. A process according to claim 3(f) wherein the suitable solvent is ethanol.

10. A compound according to claim 1 wherein R is defined as hydrogen.

11. A compound according to claim 1 wherein R is defined as methyl.

12. A compound according to claim 1 wherein R is defined as ethyl.

13. A compound according to claim 1 wherein R is defined as propyl.

14. The compound trans-(+)-1,1-diethoxy-3-methyl-3,4-epoxypentan-5-ol.

15. The compound (2S-cis)-tetrahydro-5- ethoxy-3-methylene-2-furanmethanol.

16. The compound (2S-trans)-tetrahydro-5-ethoxy-3-methylene-2-furanmethanol.

17. The compound (2S-cis)-tetrahydro-5-hydroxy-3-methylene-2-furanmethanol.

18. The compound (2S-trans)-tetrahydro-5-hydroxy-3-methylene-2-furanmethanol.

* * * * *